(12) United States Patent
Hirose

(10) Patent No.: US 6,826,971 B2
(45) Date of Patent: Dec. 7, 2004

(54) FABRICATION METHOD FOR SAMPLE TO BE ANALYZED

(75) Inventor: Yukinori Hirose, Hyogo (JP)

(73) Assignee: Renesas Technology Corp., Tokyo (JP)

( * ) Notice: Subject to any disclaimer, the term of this patent is extended or adjusted under 35 U.S.C. 154(b) by 0 days.

(21) Appl. No.: 10/176,658

(22) Filed: Jun. 24, 2002

(65) Prior Publication Data

US 2003/0097888 A1 May 29, 2003

(30) Foreign Application Priority Data

Nov. 26, 2001 (JP) ........................................ 2001-359002

(51) Int. Cl.7 ................................................ G01N 1/00
(52) U.S. Cl. ........................ 73/863; 250/304; 438/14; 438/17
(58) Field of Search ........................ 73/863; 250/304, 250/307; 438/14, 5, 10, 17

(56) References Cited

U.S. PATENT DOCUMENTS

| | | | | |
|---|---|---|---|---|
| 4,939,364 | A | * | 7/1990 | Ishitani et al. ............... 250/309 |
| 6,281,025 | B1 | * | 8/2001 | Ring et al. ..................... 438/10 |
| 6,303,399 | B1 | * | 10/2001 | Engelmann et al. .......... 438/14 |
| 6,420,722 | B2 | * | 7/2002 | Moore et al. .......... 250/559.27 |
| 2002/0024011 | A1 | * | 2/2002 | Shimizu ..................... 250/307 |
| 2002/0050565 | A1 | * | 5/2002 | Tokuda et al. .............. 250/310 |

FOREIGN PATENT DOCUMENTS

| | | |
|---|---|---|
| JP | 5-52721 | 3/1993 |
| JP | 11-108813 | 4/1999 |
| JP | 11-258130 | 9/1999 |

OTHER PUBLICATIONS

T. Ohnishi, et al, "*A New Focused–Ion–Bean Microsampling Technique for TEM Observation of Site–Specific Area's*" Proceedings from the 25th International Symposium for Testing and Failure Analysis, Nov. 14–18, 1999, pp. 449–453.

R. J. Young, et al, "*High–Yield and High–Throughput TEM Sample Preparation Using Focused Ion Bean Automation*" Proceedings from the 24th International Symposium for Testing and Failure Analysis, Nov. 15–19, 1998, pp. 329–336.

P. Malberti, et al, "*A New Back–Etch For Silicon Devices*" Proceedings from the 21st International Symposium for Testing and Failure Analysis, Nov. 6–10, 1995, pp. 257–261.

D. Corum, et al, "*Practical Applications of Backside Silicon Etching*" Proceedings from the 21st International Symposium for Testing and Failure Analysis, Nov. 6–10, 1995, pp. 263–268.

* cited by examiner

*Primary Examiner*—Hezron Williams
*Assistant Examiner*—Nashmiya Fayyaz
(74) *Attorney, Agent, or Firm*—McDermott Will & Emery LLP

(57) ABSTRACT

The semiconductor substrate is removed from a wafer or a chip wherein a defect has occurred and, thereby, the surface, which faces the substrate, that contacts the semiconductor substrate in an element formation portion is exposed. A cross section of the element formation portion is exposed through the irradiation of a focused ion beam. Furthermore, a microprober is adhered to the sample and, then, the sample including a foreign substance that is considered to be a cause of defects is detached from the element formation portion. The extracted sample is moved onto a supporting base for analysis and the sample is secured to the supporting base for analysis by forming a tungsten film. Thereby, detailed information can be gained concerning a defective portion that is located, in particular, in the vicinity of the surface of the semiconductor substrate from among defective portions that have occurred in the semiconductor device.

7 Claims, 12 Drawing Sheets

FABRICATION METHOD FOR SAMPLE TO BE ANALYZED

BACKGROUND OF THE INVENTION

1. Field of the Invention

The present invention relates to a fabrication method for a sample to be analyzed, in particular, a fabrication method for a sample to be analyzed wherein a sample for examining defective portions of a semiconductor device is fabricated.

2. Description of the Background Art

In the case that a defect occurs during the course of the manufacturing process of a semiconductor device or in the case that a defect occurs in a semiconductor device that is on the market, a defect analysis is carried out in order to determine the cause of that defect.

A fabrication method of a sample using a microsampling method and the structure of this sample shown as a fabrication method of a sample for a physical analysis used in a defect analysis by using a transmission electron microscope (hereinafter referred to as "TEM"), or the like, in, for example, Reference 1 (Japanese Patent Laying-Open No. 5-52721), Reference 2 (Japanese Patent Laying-open No. 11-258130), Reference 3 (Japanese Patent Laying-Open No. 11-108813) and Reference 4 (T. Ohnishi et al., "A New Focused-Ion-Beam Microsampling Technique for TEM Observation of Site-specific Area's", Proc. 25th Int. Symp. for Testing and Failure Analysis (1999) p. 449).

In addition, a fabrication method of a sample using a pick up method and the structure of this sample are shown as a fabrication method of a sample for a physical analysis that is used for a defect analysis in Reference 5 (R. J. Young et al., "High-Yield and High-Throughput TEM Sample Preparation Using Focused Ion Beam Automation", Proc. 24th Int. Symp. for Testing and Failure Analysis (1998) p. 329).

Furthermore, a technique for carrying out a defect analysis by means of a scanning electron microscope (hereinafter referred to as "SEM"), or the like, from the rear surface of a silicon device that is exposed by removing the silicon substrate in the device through etching is disclosed in Reference 6 (P. Malberti et al., "A new Back-Etch for Silicon Devices", Proc. 21st Int. Symp. for Testing and Failure Analysis (1995) p. 257) and in Reference 7 (D. Corum et al., "Practical Applications of Backside Silicon Etching", Proc. 21st Int. Symp. for Testing and Failure Analysis (1995) p. 263).

However, the following problems arise in the above described conventional fabrication method of a sample for defect analysis. A sample is extracted from the surface of a semiconductor device so as to include a defective portion according to the methods shown in Reference 1 to Reference 5, respectively. A multi-layered wire structure is adopted in many semiconductor devices.

Therefore, in the case that a defective portion, such as a foreign substance or a flaw, existing in the vicinity of the surface of a silicon substrate must be selectively examined, the targeted defective portion must be exposed by removing wires, layer by layer, from the wires located on the top layer in order to become visible to a SEM or to a scanning ion microscope (hereinafter referred to as "SIM").

In order to remove the wires, it becomes necessary to establish, in advance, the conditions for removal of the wires, such as the calculation of the period of etching time from the etching rate of the etchant for the wires. In addition, it takes time for the removal, itself, of the wires.

Therefore, there is a problem that a great amount of time and labor must be spent before the defective portion can be observed.

In addition, according to techniques shown in Reference 6 and Reference 7, respectively, observation can only be carried out from the rear surface of a semiconductor device. Therefore, there is a problem that information concerning the detailed structure, composition, or the like, of the defective portion, such as the three dimensional structure of the defective portion, cannot be gained.

SUMMARY OF THE INVENTION

The present invention is provided in order to solve the above described problems and the purpose thereof is to provide a fabrication method of a sample to be analyzed wherein a sample with a defective portion located, in particular, in the vicinity of the surface of a semiconductor substrate from among the defective portions that have occurred in a semiconductor device is fabricated so that detailed information of this portion can be gained.

A fabrication method of a sample to be analyzed according to one aspect of the present invention is a fabrication method of a sample to be analyzed wherein a sample is fabricated for analyzing a defect that has occurred in a semiconductor device that includes a semiconductor substrate and an element formation portion formed on this semiconductor substrate and is provided with the following steps. The semiconductor substrate is removed so as to expose the surface, which faces the substrate, that contacts the semiconductor substrate in the element formation portion. A sample body is extracted from the surface, which faces the substrate, that is exposed so that the cross section of the element formation portion is exposed. The surface of the extracted sample body on the side opposite to the surface facing the substrate is secured to a sample supporting portion and, thereby, the sample body is set on the sample supporting portion.

According to this fabrication method of a sample to be analyzed, the surface, which faces the substrate, that contacts the semiconductor substrate in the element formation portion is exposed and the cross section of the element formation portion is also exposed and, thereby, a defective portion located in the vicinity of the surface of the semiconductor substrate, in particular, can be easily observed and evaluated without sequentially removing a plurality of wires located in the upper layers.

In addition, it is preferable to provide the step of forming a protective film on the surface, which faces the substrate, that has been exposed between the step of exposing the surface facing the substrate and the step of extracting the sample body.

In this case, at the time of the detachment of the sample body by means of a focused ion beam, the detachment can be carried out without damaging the exposed surface facing the substrate.

Furthermore, one example of a preferable sample supporting portion that can be used in the step of concretely setting the sample body onto the sample supporting portion is a supporting portion of a mesh form.

Here, in the step of the extraction of the sample body, it is preferable for the sample body to be extracted to be of an order of size of microns and, thereby, a sample that includes a defective portion can be easily handled and can be analyzed in a comparatively easy manner.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Embodiment 1

Figure 1:
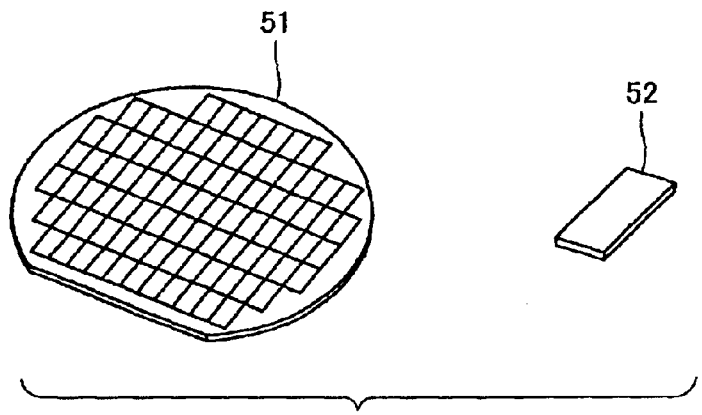
FIG. 1 is a perspective view showing one step of a fabrication method of a sample to be analyzed according to Embodiment 1 of the present invention.

A fabrication method of a sample to be analyzed according to Embodiment 1 of the present invention is described. First, as shown in FIG. 1, a wafer 51 or a chip 52 wherein a defect has occurred is prepared. In particular, in the case of a semiconductor device in a mold, it is desirable for chip 52 to be extracted by removing the molding resin in advance.

Figure 2:
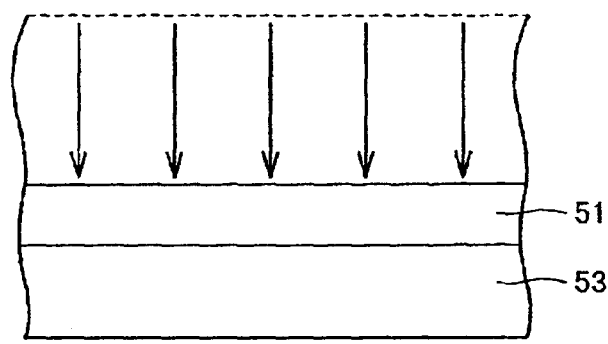
FIG. 2 is a side view showing the step that is carried out after the step shown in FIG. 1 according to Embodiment 1.

Next, as shown in FIG. 2, mechanical polishing is carried out on the rear surface opposite to the side wherein a portion (element formation portion) 53, where an element of semiconductor substrate 51 is formed, is located and, thereby, the thickness of semiconductor substrate 51 is reduced to approximately 30 $\mu$m. At this time, the mechanical polishing process may be carried out on the entire surface of semiconductor substrate 51. In addition, the mechanical polishing process may be carried out on only a specific area including a defective portion.

Here, a metal plate, or the like, may be adhered to the top surface of element formation portion 53 by using an appropriate adhesive in order to reinforce, in advance, the sample that is made thinner by polishing.

Figure 3:
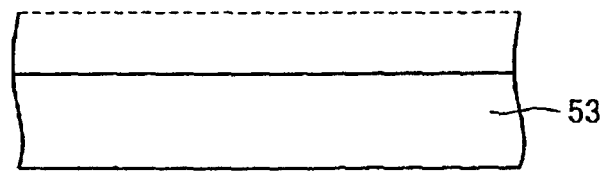
FIG. 3 is a side view showing the step that is carried out after the step shown in FIG. 2 according to Embodiment 1.

Next, as shown in FIG. 3, a portion of remaining semiconductor substrate 51 is removed by using an appropriate etchant. In the case that semiconductor substrate 51 is a silicon substrate, for example, it can be removed by using a strong alkaline solution such as a tetraethyl-ammonium hydroxide, which is cited in Reference 6 and Reference 7.

Figure 4:
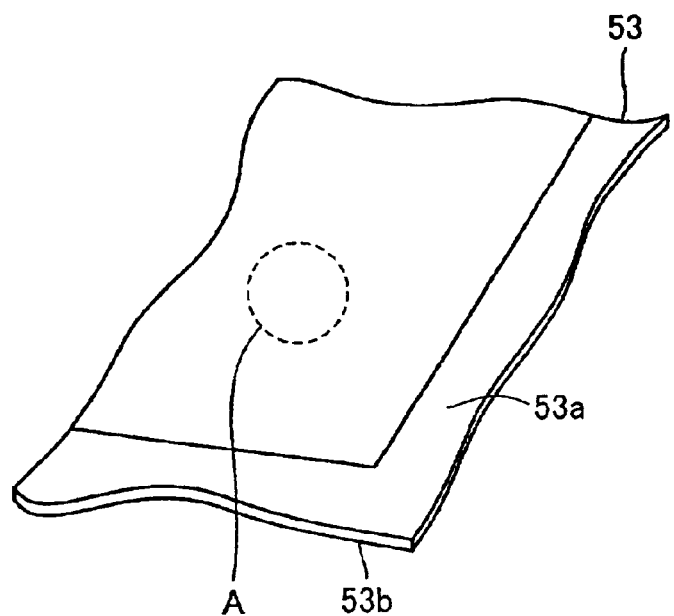
FIG. 4 is a perspective view of a portion showing the step that is carried out after the step shown in FIG. 3 according to Embodiment 1.
Figure 5:
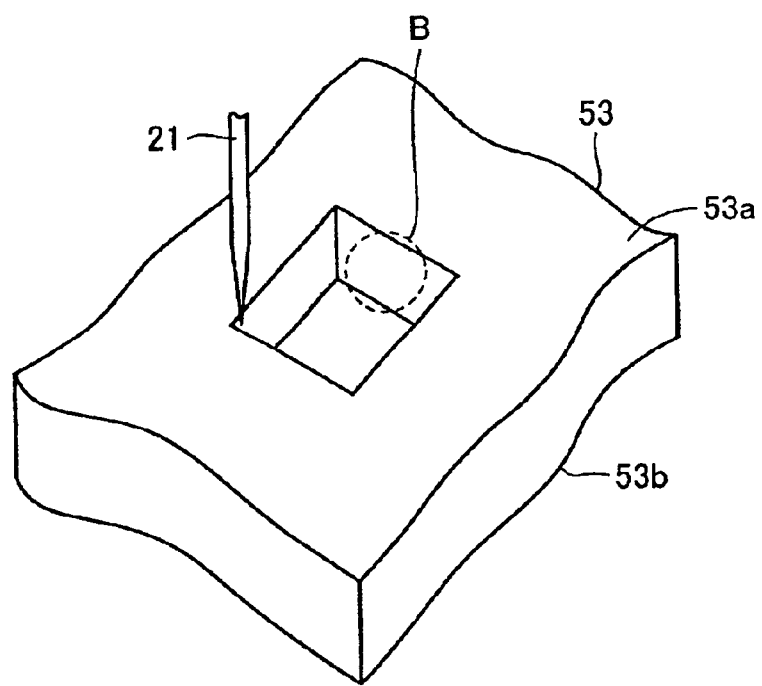
FIG. 5 is a perspective view of a portion showing the step that is carried out after the step shown in FIG. 4 according to Embodiment 1.

Thereby, as shown in FIG. 4, surface 53a of element formation portion 53, which faces the substrate, that contacts semiconductor substrate 51 is exposed. Next, this element formation portion 53 is introduced within a focused ion beam unit (not shown). Then, an area A wherein a defective portion exists in element formation portion 53 is irradiated with a focused ion beam 21, as shown in FIG. 5.

Figure 6:
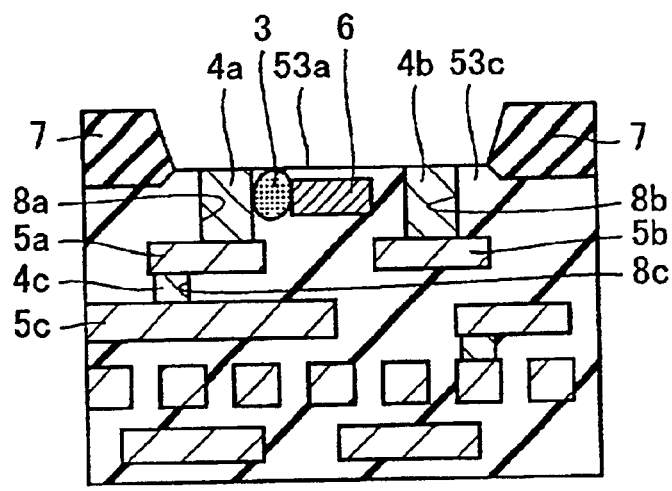
FIG. 6 is a cross sectional view of an element formation portion that is exposed in the step shown in FIG. 5 according to Embodiment 1.

A cross section 53c of an element that includes, for example, a gate electrode 6, plugs 4a to 4c formed in contact holes 8a to 8c, respectively, a wire 5a connected to plug 4a and plug 4c, a wire 5b connected to plug 4b and a wire 5c connected to plug 4c is exposed on one cross sectional area B of element formation portion 53 that is exposed through the irradiation of focused ion beam 21, as shown in FIG. 6. Furthermore, a foreign substance 3, considered to be a cause of defects, is exposed between gate electrode 6 and plug 4a.

Figure 7:
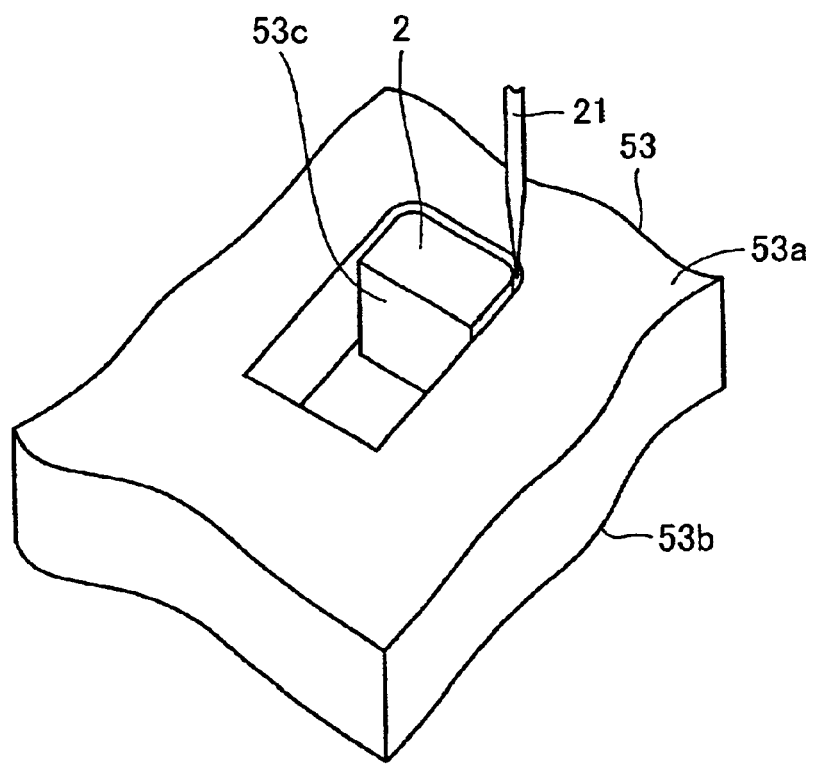
FIG. 7 is a perspective view of a portion showing the step that is carried out after the step shown in FIG. 5 according to Embodiment 1.
Figure 8:
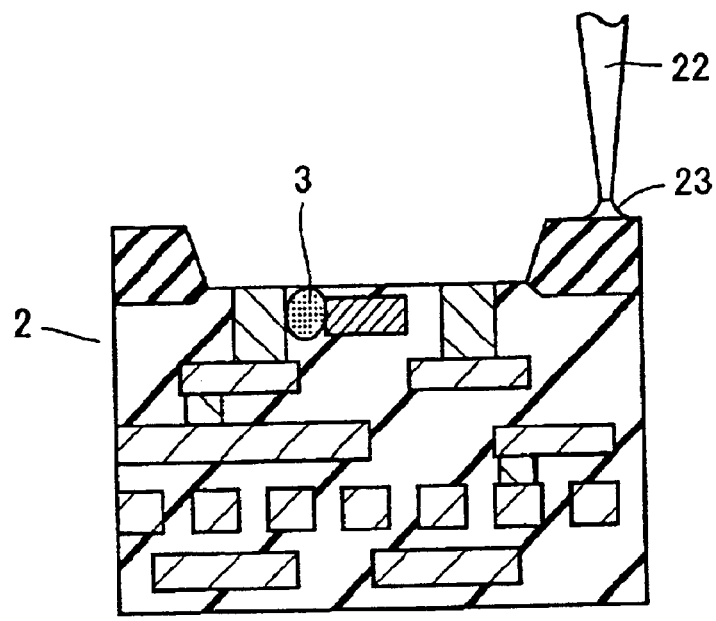
FIG. 8 is a cross sectional view showing the step that is carried out after the step shown in FIG. 7 according to Embodiment 1.
Figure 9:
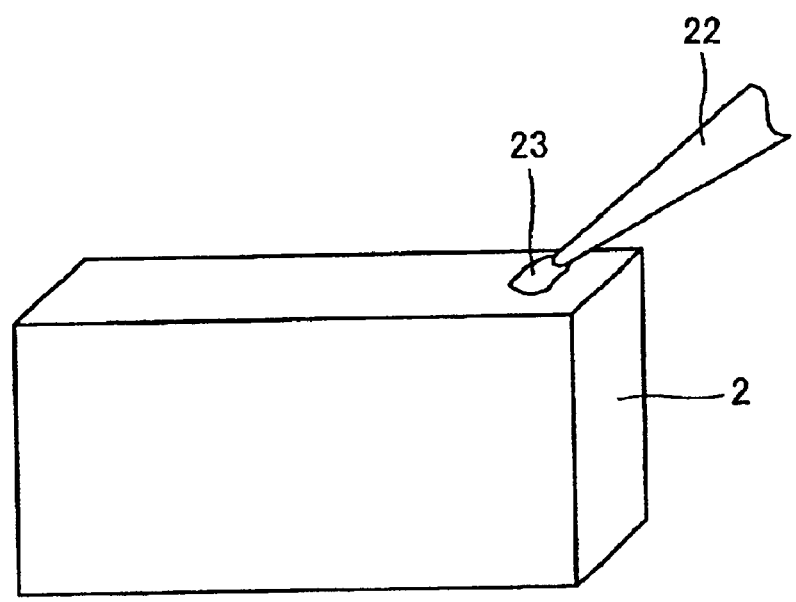
FIG. 9 is a perspective view of a portion showing the step shown in FIG. 8 according to Embodiment 1.

Next, as shown in FIG. 7, a sample 2 that includes foreign substance 3, considered to be a cause of defects, is detached from element formation portion 53 by means of irradiation by a focused ion beam 21. At this time, as shown in FIGS. 8 and 9, a tungsten film 23 is formed in the condition wherein a microprober 22 is made to contact sample 2 in advance so that microprober 22 is adhered to sample 2. Thereby, sample 2, which has been detached from element formation portion 53, can be easily extracted. Here, at the time of the detachment of the sample, a focused ion beam may be irradiated so as to pass through element formation portion 53.

It is preferable for the size of detached sample 2 to be of an order of microns and, thereby, the sample that includes a defective portion can be easily handled and can be analyzed in a comparatively easy manner. Here, the order of microns mentioned in this specification depends on the size of the defective portion and, in general, means that the size of the defective portion, including the peripheral portions thereof, is up to approximately several tens of $\mu$ms.

Here, a microprober 22 is pre-installed within the focused ion beam unit. In addition, tungsten film 23 is formed through the irradiation of Ga$^+$ ions in the form of a focused ion beam while a tungsten hexa-carbonyl [$W(CO)_6$] gas is allowed to flow within the focused ion beam unit.

Next, extracted sample 2 is moved onto a supporting base 25 for analysis and, then, sample 2 is secured to supporting base 25 for analysis by forming, for example, a tungsten film 23. Next, mircroprober 22 is detached from sample 2 by using an etching function that is pre-installed within the focused ion beam unit.

Figure 10:
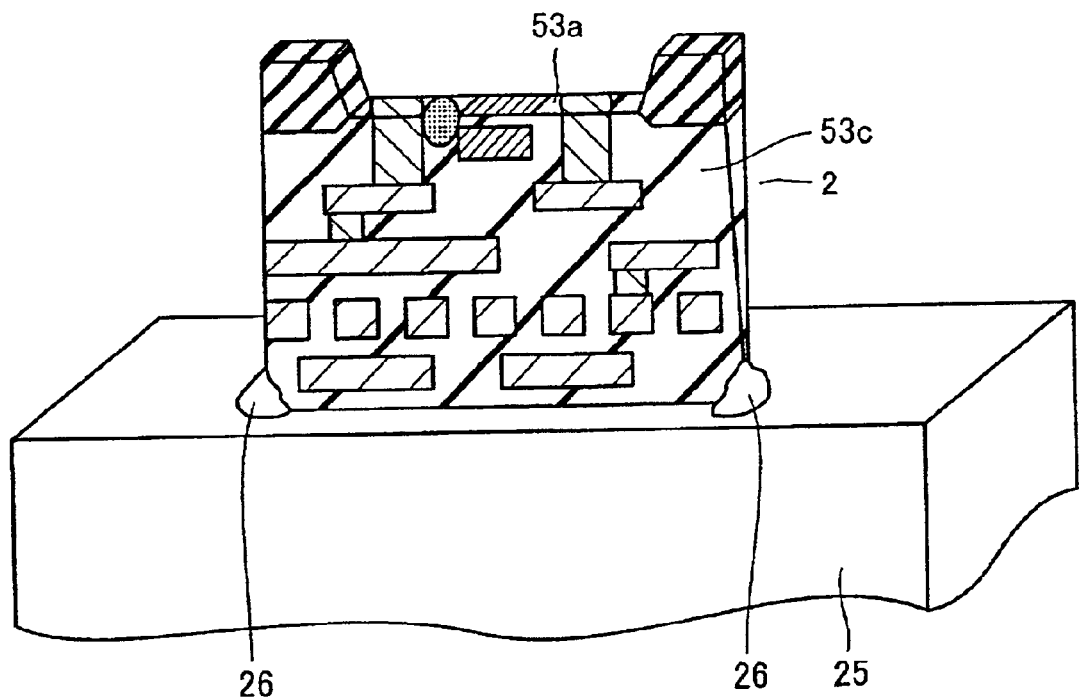
FIG. 10 is a perspective view of a portion showing the step that is carried out after the step shown in FIG. 9 according to Embodiment 1.

Thereby, as shown in FIG. 10, sample 2 secured to supporting base 25 for analysis is gained. After that, sample 2 secured to supporting base 25 for analysis is introduced into an appropriate analysis unit so as to carry out a defect analysis.

In sample 2 fabricated in such a manner as shown in FIG. 10, surface 53a, which faces the substrate, that contacts semiconductor substrate 51 in element formation portion 53 is exposed and cross section 53c of element formation portion 53 is also exposed.

Thereby, a foreign substance, or the like, that exists in proximity to gate electrode 6 or that is in the general vicinity of the surface of semiconductor substrate 51 and that is assumed to be a cause of defects can be observed and evaluated without sequentially removing a plurality of wires located above the gate electrode. One example of this evaluation is described in detail hereinafter.

Figure 11:
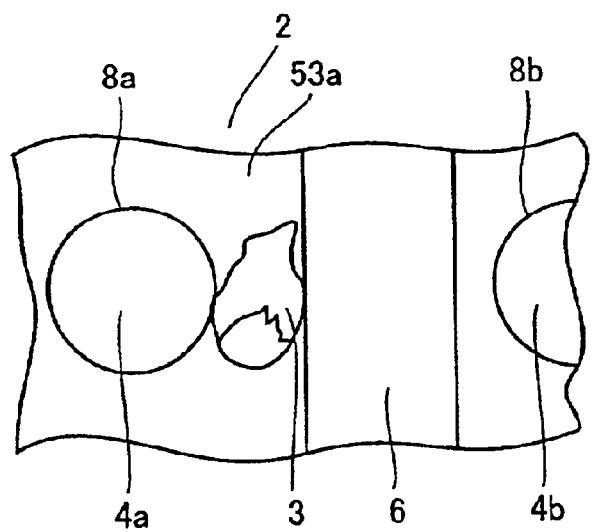
FIG. 11 is one schematic plan view showing a surface, which faces the substrate, that includes a defective portion according to Embodiment 1.
Figure 12:
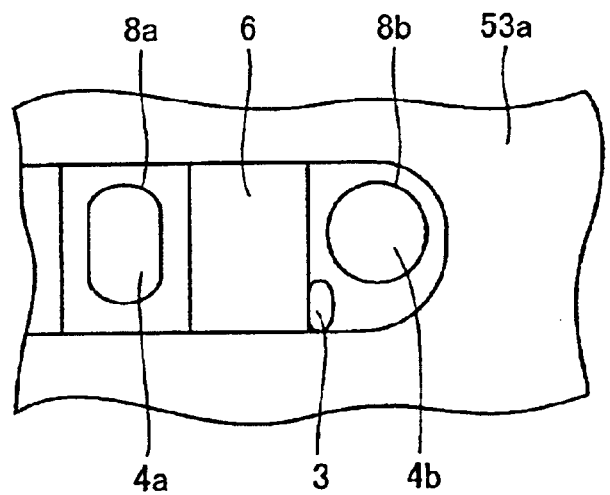
FIG. 12 is another schematic plan view showing a surface, which faces the substrate, that includes a defective portion according to Embodiment 1.

Here, as described in the step shown in FIG. 5, area A wherein a defective portion of element formation portion 53 exists is irradiated with focused ion beam 21. As shown in FIGS. 11 and 12, the portion wherein foreign substance 3 exists as the defective portion is observed as a stain or as a pattern defect. Such a stain or pattern defect can be easily observed by slightly raising the acceleration voltage (for example, to 20 KV) at the time of, for example, SEM observation. In addition, it is desirable to carry out etching on surface 53a, which faces the substrate, of element formation portion 53 by means of fluoric acid so that information concerning the inside of element formation portion 53 can be made more easily attainable. Thus, sample 2 can be fabricated so that a defective portion can be easily discovered and so that such a defective portion is included in the sample.

Next, one modified example of a fabrication of a sample to be analyzed is described. As described above, area A wherein a defective portion of element formation portion 53 exists is irradiated with a focused ion beam in the step shown in FIG. 5. Element formation portion 53 is irradiated with a focused ion beam and, thereby, damage may be caused to surface 53a, which faces the substrate.

Figure 13:
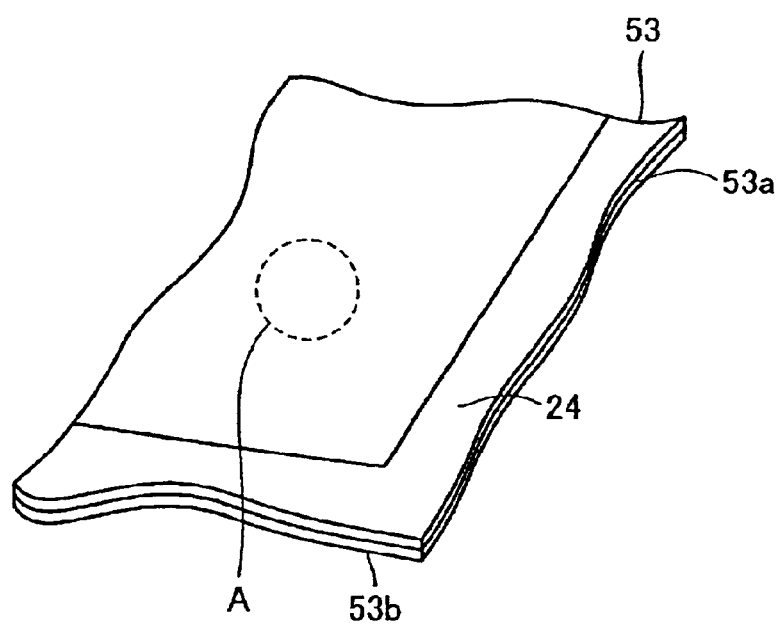
FIG. 13 is a perspective view of a portion showing one step of a fabrication method of a sample according to one modified example of Embodiment 1.
Figure 14:
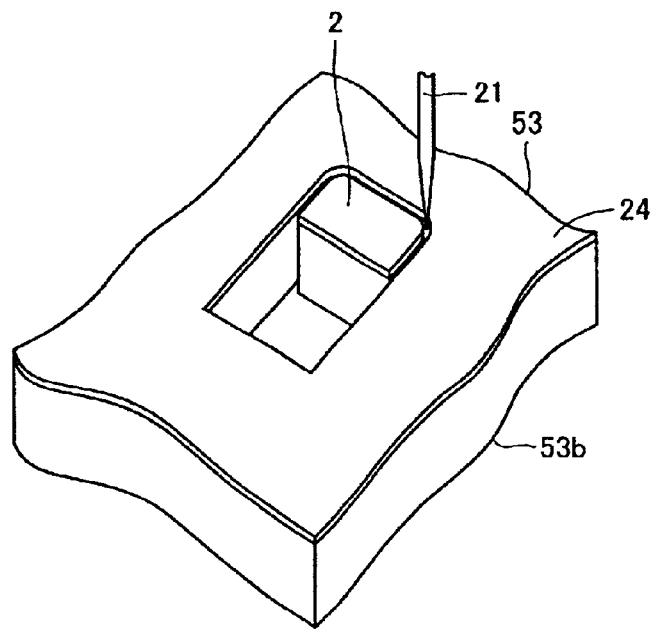
FIG. 14 is a perspective view of a portion showing the step that is carried out after the step shown in FIG. 13 according to Embodiment 1.
Figure 15:
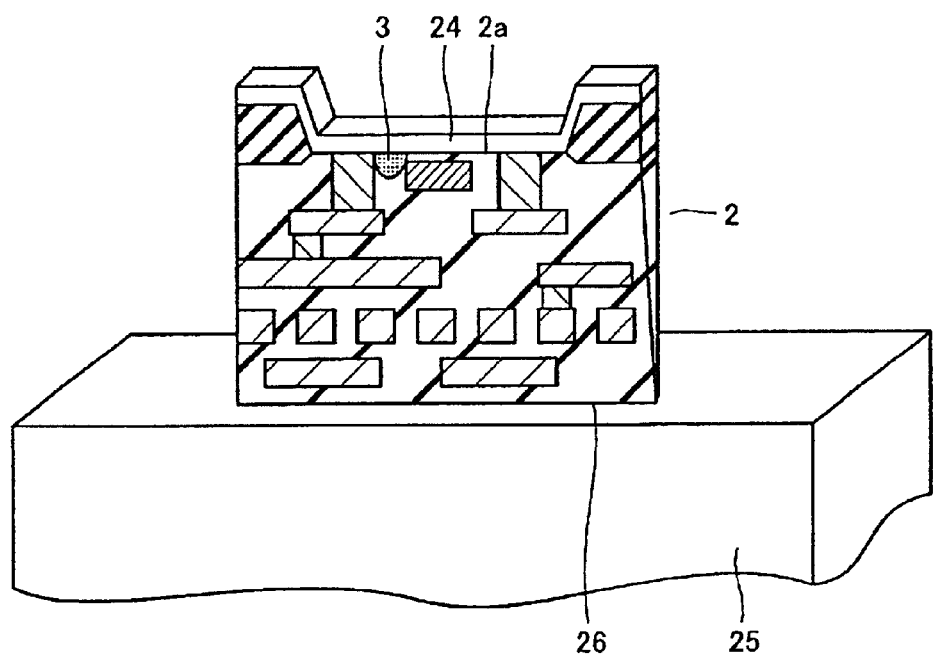
FIG. 15 is a perspective view of a portion showing the step that is carried out after the step shown in FIG. 14 according to Embodiment 1.

Then, as shown in FIG. 13, a hydrocarbon-base film 24 is formed on surface 53a, which faces the substrate, in a plasma film deposition unit after the exposure of surface 53a, which faces the substrate. After that, as shown in FIG. 14, cross section 53c of element formation portion 53 is exposed through the irradiation of focused ion beam 21 under the condition wherein hydrocarbon-based film 24 is formed. After that, the same method as the above described method is followed so as to gain sample 2 to be analyzed, as shown in FIG. 15, wherein hydrocarbon-based film 24 is formed on surface 53a, which faces the substrate.

According to this method, hydrocarbon-based film 24 is formed on surface 53a, which faces the substrate, so that damage to surface 53a, which faces the substrate, is prevented from occurring at the time of the irradiation of focused ion beam 21 and, thereby, the defective portion of sample 2 to be analyzed can be clearly observed.

Figure 16:
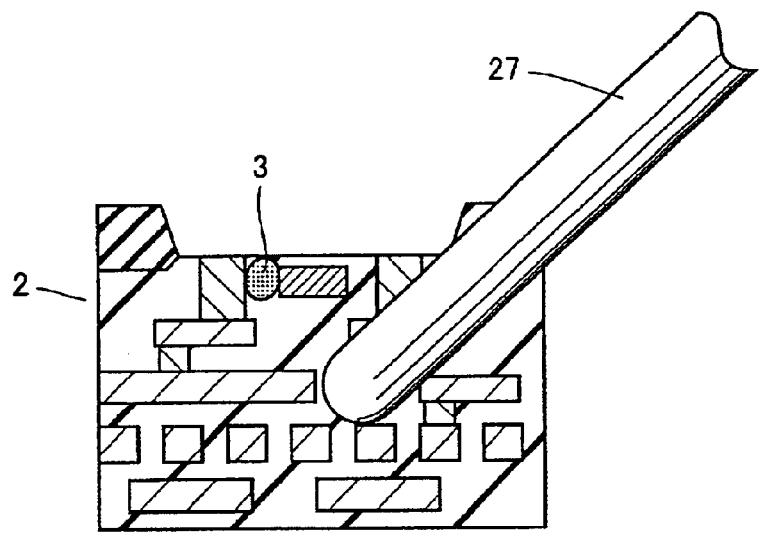
FIG. 16 is a perspective view of a portion showing one step of a fabrication method of a sample according to another modified example of Embodiment 1.

Next, another modified example of the fabrication method of a sample to be analyzed is described. First, after the step of detaching the above described sample 2, shown in FIG. 7, from element formation portion 53, an insulated mircroprober 27 provided within the focused ion beam unit is allowed to contact sample 2, as shown in FIG. 16. Sample 2 is attached to this mircroprober 27 due to static electric force that works on mircroprober 27. Then, attached sample 2 is extracted by mircroprober 27.

Figure 17:
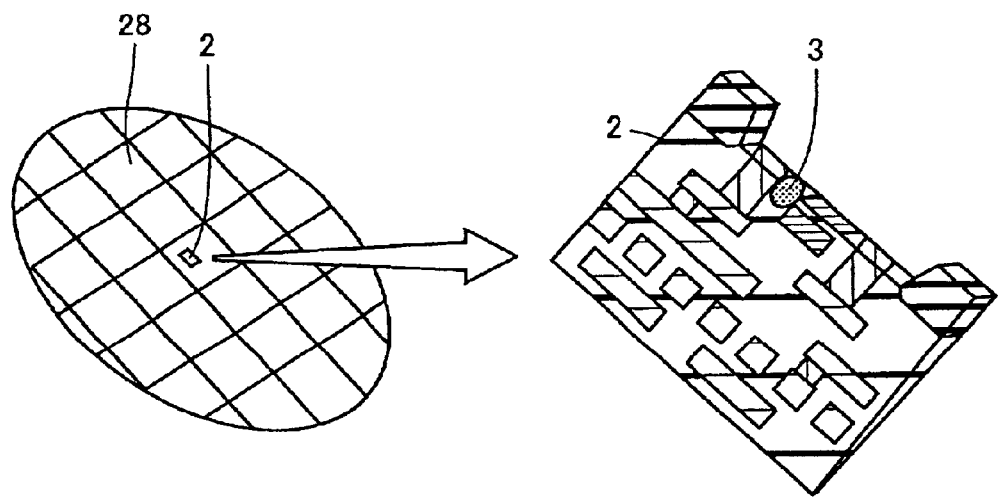
FIG. 17 is a perspective view of a portion showing the step that is carried out after the step shown in FIG. 16 according to Embodiment 1.

Next, as shown in FIG. 17, extracted sample 2 is attached to a mesh 28 for holding a sample to be analyzed. Mesh 28 for holding a sample to be analyzed is formed of a metal grid, for example, copper, and an organic thin film, such as carbon, having a film thickness of approximately 10 nm, is formed on the surface thereof. It is preferable for the intervals of this mesh 28 for holding a sample to be analyzed to be in the range of from approximately 50 $\mu$m to 500 $\mu$m.

Figure 18:
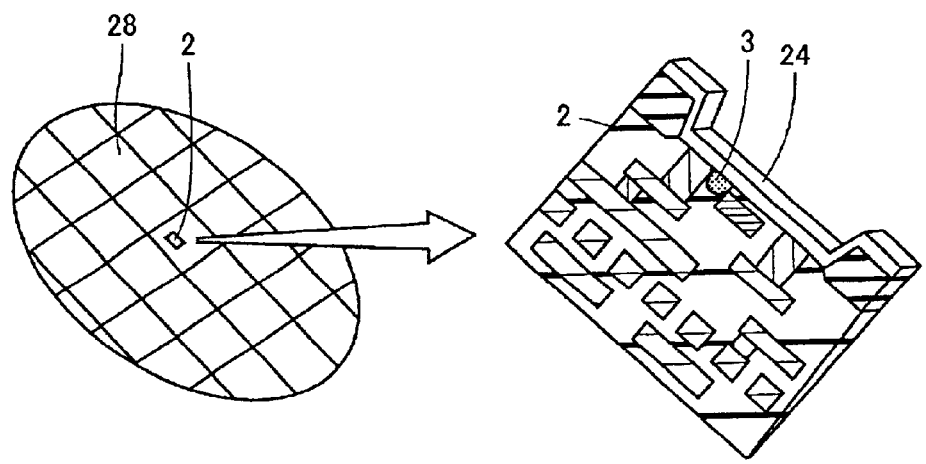
FIG. 18 is a perspective view of a portion showing one step of a fabrication method of a sample according to still another modified example of Embodiment 1.

Here, a film of hydrocarbon may be formed through the same steps as the above described steps shown in FIGS. 13 and 14 in order to prevent the damage due to focused ion beam 21. In this case, as shown in FIG. 18, a sample is gained wherein a hydrocarbon film 24 is formed on the surface facing the substrate.

Embodiment 2

An example of an analysis method of a sample fabricated according to the above described method is described in Embodiment 2 of the present invention.

Figure 19:
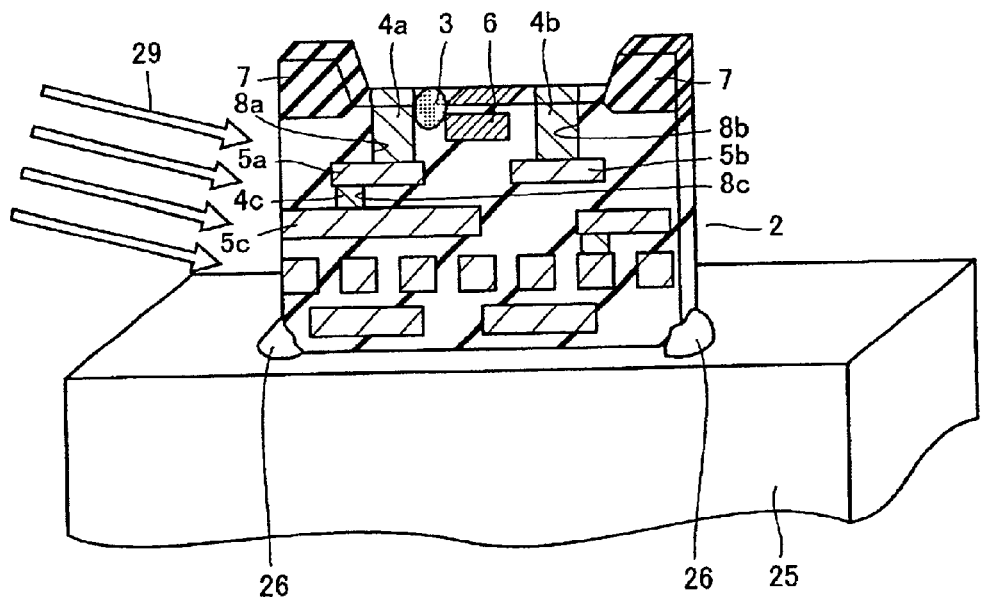
FIG. 19 is a perspective view showing an analysis method according to Embodiment 2 of the present invention.

A sample fabricated according to the above described method is introduced into, for example, an Auger electron spectrometer. Then, as shown in FIG. 19, introduced sample 2 is irradiated with an inactive ion flow 29, such as of argon ions. Sample 2 is irradiated with inactive ion flow 29 and, thereby, sputtering is carried out on the cross section of exposed sample 2. In addition, Auger electrons based on the elements forming element formation portion 53 are emitted from the exposed cross section.

Figure 20:
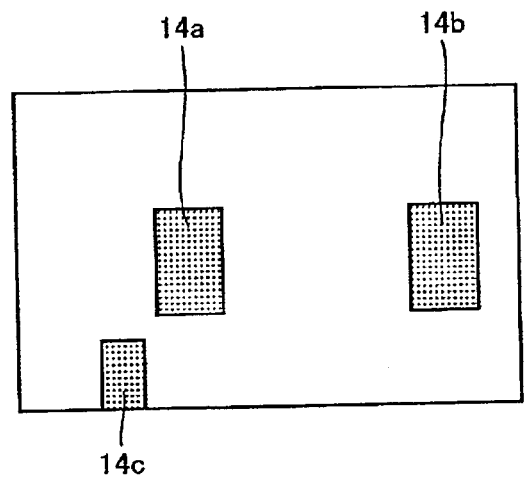
FIG. 20 is the first diagram showing a pattern of Auger electrons according to Embodiment 2.
Figure 21:
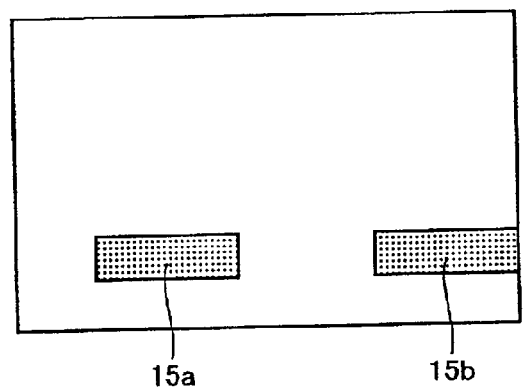
FIG. 21 is the second diagram showing the pattern of Auger electrons according to Embodiment 2.

Next, an example of a type of Auger electrons observed in such a manner is herein described. First, patterns 14a to 14c of Auger electrons gained by observing Auger electrons based on, for example, tungsten that forms plugs 4a to 4c at a specific time t are respectively shown in FIG. 20. Patterns 15a and 15c of Auger electrons gained by observing Auger electrons based on, for example, aluminum that forms wires 5a and 5c at a specific time t are respectively shown in FIG. 21.

Figure 22:
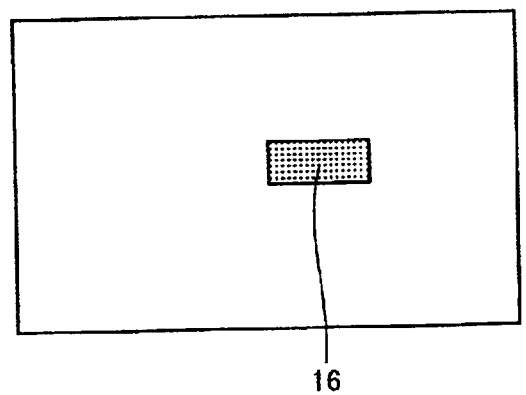
FIG. 22 is the third diagram showing the pattern of Auger electrons according to Embodiment 2.
Figure 23:
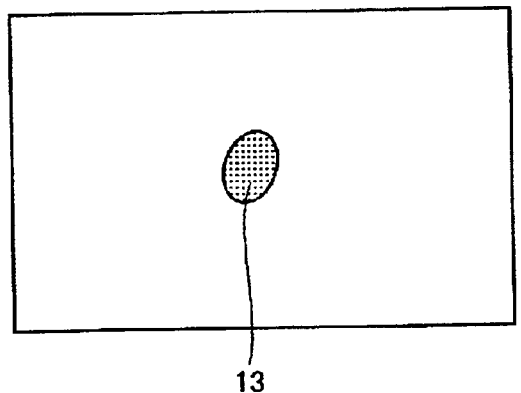
FIG. 23 is the fourth diagram showing the pattern of Auger electrons according to Embodiment 2.

A pattern 16 of Auger electrons gained by observing Auger electrons based on, for example, silicon that forms gate electrode 6 at a specific time t is shown in FIG. 22. A pattern 13 of Auger electrons gained by observing Auger electrons based on Fe, for example, or the like, that forms foreign substance 3, assumed to be a cause of defects, at a specific time t is shown in FIG. 23.

A two dimensional map of Auger electrons based on a specific element is observed at a specific time t in such a manner and, thereby, information concerning the elements that form the exposed surface of sample 2 at time t can be gained.

Furthermore, sputtering is carried out on the cross section of exposed sample 2 over a period of time and, thereby, a new surface is always exposed in sample 2. Thereby, a pattern of Auger electrons from the exposed surface after the sputtering is carried out for a period of time Δt is observed in the same manner as in the case at time t so as to so that a pattern of Auger electrons is observed.

Figure 24:
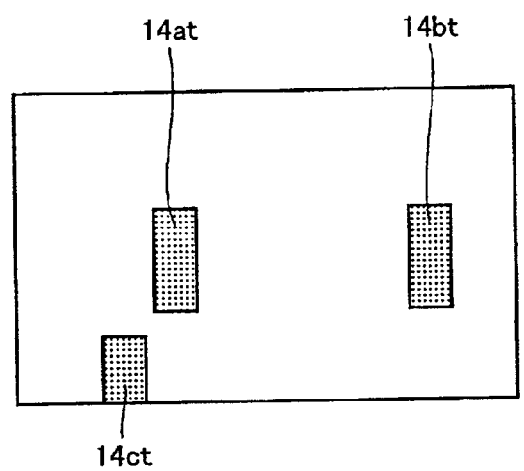
FIG. 24 is the fifth diagram showing the pattern of Auger electrons according to Embodiment 2.
Figure 25:
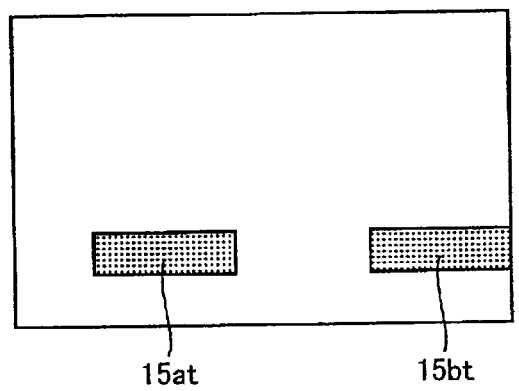
FIG. 25 is the sixth diagram showing the pattern of Auger electrons according to Embodiment 2.

First, FIG. 24 shows patterns 14at to 14ct, respectively, of Auger electrons gained by observing Auger electrons based on tungsten that forms plugs 4a to 4c at time t+Δt. FIG. 25 shows patterns 15at and 15ct, respectively, of Auger electrons gained by observing Auger electrons based on aluminum that forms wires 5a and 5c at time t+Δt.

Figure 26:
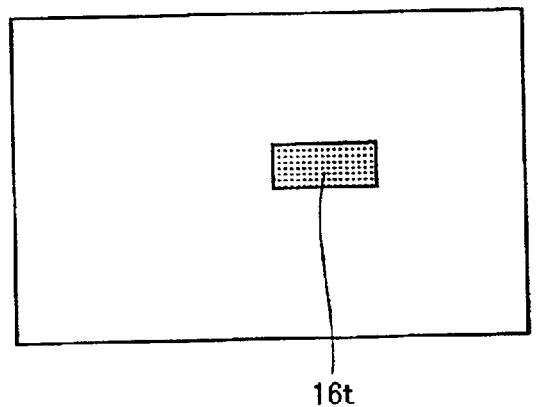
FIG. 26 is the seventh diagram showing the pattern of Auger electrons according to Embodiment 2.
Figure 27:
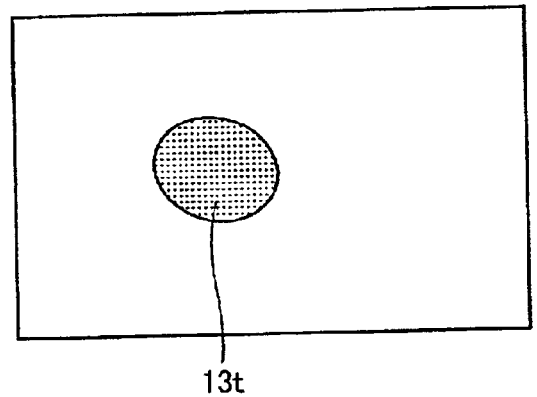
FIG. 27 is the eighth diagram showing the pattern of Auger electrons according to Embodiment 2.

FIG. 26 shows a pattern 16t of Auger electrons gained by observing Auger electrons based on silicon that forms gate electrode 6 at time t+Δt. FIG. 27 shows a pattern 13t of Auger electrons gained by observing Auger electrons based on Fe, or the like, that forms foreign substance 3 at time t+Δt.

Thus, Auger electrons in the cross section of the sample exposed in a chronological manner are observed for every constant period of time so that these patterns of Auger electrons are linked in order to gain information concerning the three dimensional structure of sample 2, which includes a defective portion.

Figure 28:
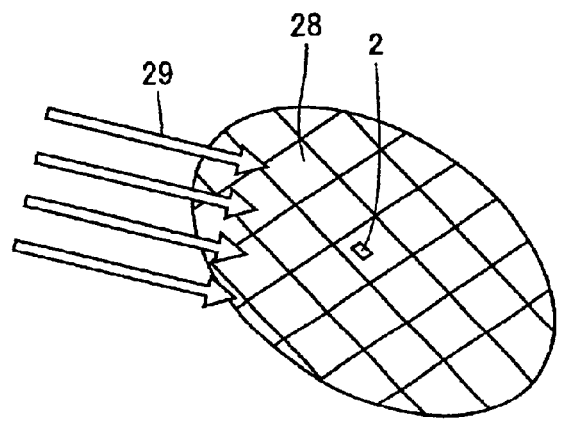
FIG. 28 is another perspective view showing the analysis method according to Embodiment 2.

Here, in the case that sample 2 is secured to mesh 28 for holding a sample to be analyzed, three dimensional information concerning the components elements of a defective portion can be gained by irradiating sample 2 with inactive ion flow 29, as shown in FIG. 28.

An example is cited to describe the case wherein information concerning the three dimensional structure of a sample is gained based on information concerning the component elements of the sample including a defective portion gained through Auger electron spectroscopy according to the above described analysis method. In addition to this, it is possible to analyze the structure of sample 2 by means of the TEM. In particular, in the case that sample 2 is secured to a sample supporting base, the sample can, if necessary, be made thinner as a sample for the TEM within the focused ion beam unit.

Furthermore, an energy dispersive-type X-ray analysis EDX (energy dispersive X-ray) is, additionally, used so that the component elements of a microscopic segment of a defective portion can be analyzed. Moreover, electron energy loss spectroscopy EELS may be used so that an element analysis, or the like, of a microscopic area can be carried out.

Alternatively, a secondary ion mass spectroscopy SIMS may be used so that an element analysis of a foreign substance, or the like, that is assumed to be in a defective portion can be carried out. In addition, a scanning probe microscope SPM may be used so that the atomic condition or electron condition of a defective portion can be observed.

As described above, surface 53a, which faces the substrate, that contacts the semiconductor substrate in element formation portion 53 is exposed and cross section 53c of element formation portion 53 is exposed according to the above described fabrication method of a sample and, thereby, a defective portion located, in particular, in the vicinity of the surface of the semiconductor substrate can be easily observed and evaluated without sequentially removing a plurality of wires located in the upper layers so that three dimensional information of the component elements in, for example, a defective portion, can be gained.

The Embodiments discloses herein should be considered to be illustrative from all points of view and are not limitative. The present invention is defined not by the above described but by the claims and is intended to include meanings equivalent to the claims and all of the modifications within the scope.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A fabrication method of a sample to be analyzed, wherein a sample for analyzing a defect that has occurred in a semiconductor device that includes a semiconductor substrate and an element formation portion formed in this semiconductor substrate is fabricated, comprising the steps of:

removing said semiconductor substrate so as to expose a surface, the element formation portion, said surface faces the substrate and contacts said semiconductor substrate;

forming a protective film on said exposed surface facing the substrate;

extracting a sample body from said exposed surface, which faces the substrate, so that a cross section of said element formation portion is exposed, wherein said extracted sample body includes a defect and said protective film covers said defect; and setting said extracted sample body onto a sample supporting portion by securing a surface of said sample body, on a side opposite to said exposed surface facing the substrate, to said sample supporting portion.

2. The fabrication method of a sample to be analyzed according to claim 1, wherein a supporting portion of a mesh form is used as said sample supporting portion in said step of setting said sample body onto said sample supporting portion.

3. The fabrication method of claim 2, wherein said mesh is formed of a metal grid and an organic thin film.

4. The fabrication method of claim 1, wherein the step of removing said semiconductor substrate comprises mechanically polishing said substrate.

5. The fabrication method of claim 4, wherein the step of removing said semiconductor substrate further comprises etching said substrate.

6. The fabrication method of claim 1, wherein said step of forming a protective film comprises forming a hydrocarbon-based film.

7. The fabrication method of claim 1, wherein said step of extracting a sample body comprises irradiation of said surface by a focused ion beam.

* * * * *